(12) United States Patent
Andjelic et al.

(10) Patent No.: US 7,968,656 B2
(45) Date of Patent: Jun. 28, 2011

(54) ABSORBABLE COPOLYESTERS OF POLY(ETHOXYETHYLENE DIGLYCOLATE) AND GLYCOLIDE

(75) Inventors: Sasa Andjelic, Nanuet, NY (US); Jiango Jack Zhou, Bethlehem, PA (US); Modesto Erneta, Princeton Junction, NJ (US); Michel Gensini, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 395 days.

(21) Appl. No.: 12/107,591

(22) Filed: Apr. 22, 2008

(65) Prior Publication Data

US 2009/0104276 A1 Apr. 23, 2009

Related U.S. Application Data

(63) Continuation-in-part of application No. 11/693,118, filed on Mar. 29, 2007, and a continuation-in-part of application No. 11/554,675, filed on Oct. 31, 2006, now Pat. No. 7,652,127.

(51) Int. Cl.
*C08G 63/00* (2006.01)
*C08G 59/00* (2006.01)

(52) U.S. Cl. .............. 525/437; 264/210.8; 424/426; 424/497; 442/351; 528/271; 528/272; 528/300; 528/354

(58) Field of Classification Search .............. 264/210.8; 424/426, 497; 442/351; 528/271, 272, 300, 528/354
See application file for complete search history.

(56) References Cited

U.S. PATENT DOCUMENTS

| | | | |
|---|---|---|---|
| 3,942,532 A | 3/1976 | Hunter et al. | |
| 4,048,256 A | 9/1977 | Casey et al. | |
| 4,080,969 A | 3/1978 | Casey et al. | |
| 4,095,600 A | 6/1978 | Casey et al. | |
| 4,122,129 A | 10/1978 | Casey et al. | |
| 4,343,788 A | 8/1982 | Mustacich et al. | |
| 5,644,002 A | 7/1997 | Cooper et al. | |
| 5,719,256 A | 2/1998 | Tamai et al. | |
| 6,355,772 B1 * | 3/2002 | Gruber et al. | 528/354 |
| 7,652,127 B2 * | 1/2010 | Andjeli | 528/272 |
| 7,754,233 B2 * | 7/2010 | Andjelic et al. | 424/423 |
| 7,868,127 B2 | 1/2011 | Andjelic et al. | |

| | | | |
|---|---|---|---|
| 2005/0048124 A1 | 3/2005 | Sarangapani | |
| 2006/0051398 A1 | 3/2006 | Andjelic et al. | |
| 2008/0103285 A1 * | 5/2008 | Andjelic et al. | 528/300 |
| 2008/0243101 A1 * | 10/2008 | Andjelic et al. | 604/506 |

FOREIGN PATENT DOCUMENTS

| | | |
|---|---|---|
| EP | 0 807 653 | 11/1997 |
| WO | 03043593 | 5/2003 |
| WO | 2006125098 | 11/2006 |
| WO | 2006125099 | 11/2006 |
| WO | 2006125121 | 11/2006 |
| WO | 2006125125 | 11/2006 |
| WO | WO 2006/125098 A | 11/2006 |
| WO | 2008 055086 A2 | 8/2008 |
| WO | 2009 042882 A1 | 4/2009 |

OTHER PUBLICATIONS

International Search Report dated May 9, 2008 for International Appln. No. PCT/US2007/082773.

Vogt, F.G. et al., "Structural Analysis of Polymorphism and Solvation in Tranilast", Journal of Pharmaceutical Sciences, vol. 94, No. 3, pp. 651-665 (2005).

Ouchi, Tatsuro, et al., "Encapsulation and/or Release Behavior of Bovine Serum Albumin within and from Polylactide-Grafted Dextran Microspheres", Macromolecular Bioscience, vol. 4, pp. 458-463 (2004).

Nam, Y.S. et al., "Protein loaded biodegradable microspheres based on PLGA-protein bioconjugates", Journal of Microencapsulation, vol. 16, No. 5, pp. 625-637 (1999).

Kawashima, Y. et al., "Preparation of multiple unit hollow microspheres (microballoons) with acrylic resin containing tranilast and their drug release characteristics (in vitro) and floating behavior (in vivo)", Journal of Controlled Release, vol. 16, pp. 279-288 (1991).

* cited by examiner

*Primary Examiner* — Terressa M Boykin
(74) *Attorney, Agent, or Firm* — Roberts Mlotkowski Safran & Cole, P.C.

(57) ABSTRACT

A semi-crystalline, absorbable copolyester composition comprising the reaction product of a polycondensation polyester and at least one lactone, wherein the polycondensation polyester comprises the reaction product of diglycolic acid and/or a derivative thereof and diethylene glycol; and the copolyester comprises about 30 to 60% by weight of the polycondensation polyester based on the total weight of the copolyester. Also medical devices such as absorbable sutures comprising such copolyesters and absorbable microspheres comprising such copolyesters and methods of making of such absorbable microspheres. Additionally, a method of melt blowing an absorbable copolyester composition and a nonwoven construct are disclosed.

15 Claims, No Drawings

ABSORBABLE COPOLYESTERS OF POLY(ETHOXYETHYLENE DIGLYCOLATE) AND GLYCOLIDE

CROSS-REFERENCE TO RELATED APPLICATIONS

This application is a Continuation-in-Part of application Ser. No. 11/693,118 filed on Mar. 29, 2007, which is a Continuation-in-Part of application Ser. No. 11/554,675 filed on Oct. 31, 2006, the contents of which are hereby incorporated by reference in their entirety.

FIELD OF THE INVENTION

The present invention relates to a composition comprising a semi-crystalline, absorbable copolyester comprising the reaction product of a polycondensation polyester and at least one lactone, more specifically, a semi-crystalline absorbable copolyester comprising the reaction product of poly(ethoxyethylene diglycolate) and glycolide, where the copolyester comprises about 30 to 60% by weight of the poly(ethoxyethylene diglycolate) based on the total weight of the copolyester. In addition, the present invention relates to absorbable medical devices (e.g., sutures, meshes and microspheres) comprising such copolyesters and particularly to a method of making absorbable microspheres.

BACKGROUND OF THE INVENTION

Mechanical properties of a medical device can be made to vary depending on the end use application for the device. For example, it is often desirable for surgical sutures to exhibit mechanical strength, such as straight tensile strength and knot tensile strength. One technique for producing surgical sutures having these desired properties is to utilize polymers having some degree of crystallinity. Specifically, the crystalline or ordered structure of the polymer imparts strength to a medical device produced therefrom, including but not limited to a surgical suture, surgical mesh, surgical staple, hemostatic clip, and the like.

In general, however, the greater the crystallinity of an absorbable polymer, the slower the rate of the absorption will be. Therefore, in those applications where an absorbable medical device is desired, there is a need to balance the level of crystallinity of the polymer against the absorbability thereof. For example, there are certain applications where there is a need for an absorbable medical device to absorb quickly, such as episiotomy and plastic surgical applications, where fast absorption of the medical device is highly desirable to improve patient comfort and to achieve aesthetic outcomes.

Several approaches to increase the absorption or hydrolysis rate of absorbable polymers are known. For example, one approach is to lower the crystallinity of the polymer to enhance the absorption or hydrolysis rate thereof. This may be done by randomizing the chemical structure of the polymer using, for example, different lactones in the copolymerization step to reduce the overall crystallinity of the polymer. However, the use of lactones to disrupt crystallinity has limited impact due to the considerably higher hydrophobicity of lactone, causing the resultant polymer and medical device to be more hydrophobic, and absorption or hydrolysis to occur more slowly. In addition, lowering the level of crystallinity of the polymer may adversely affect the physical properties of the medical device prepared therefrom.

A second approach to increase the absorption or hydrolysis rate of synthetic absorbable polymers is to add a non-absorbable hydrophilic moiety, e.g. a polyether such as polyethylene glycol (PEG), to increase the hydrophilicity of the absorbable polymer. However, such approach will result in poor mechanical properties of the medical device (e.g. tensile strength and modules) due to the general chemical structure of aliphatic polyethers, and the addition of PEG moieties will reduce the overall crystallinity of the polymers.

A third approach is to use a pre-degraded synthetic absorbable polymer. For example, an absorbable polymer may be subjected to a hydration step or gamma irradiated to initiate the hydrolysis of the absorbable polymer, thereby resulting in a pre-degraded product. However, problems arising with the use of a pre-degraded synthetic absorbable polymer include difficulty in controlling the quality and stability of the pre-degraded polymer. More specifically, it may be difficult to achieve reproducible levels of pre-degradation in the final product.

In another example, it may be desirable for medical devices to be in the form of an injectable composition, i.e., as a filler for soft tissue augmentation, or in combination with a drug, i.e., as a drug delivery carrier. For example, if the injectable composition or drug delivery carrier is comprised of microspheres, it is desirable for the microspheres to exhibit certain properties, i.e., the ability to pass through a small needle for injection subcutaneously or intradermally, or delivery in the peritoneal or pelvic cavity, without aggregating or agglomerating under pressure, thereby avoiding clogging of a delivery device such as a needle; and the ability to retain their distinct spherical shape without aggregating or agglomerating (hereinafter referred to as "dimensional stability"), upon manufacture, storage and physical transport. Furthermore, in some situations it may be desirable for these microspheres to retain their distinct spherical shape after implantation, to avoid agglomeration of the microspheres subcutaneously or intradermally, which would produce an unnatural appearance in the skin. Finally, if the microspheres are used as drug delivery carriers, it is desirable for the microsphere to attain homogeneous encapsulation of pharmaceutical substances, while having sustained and controlled release property.

U.S. Patent Publication 2006/0051398 assigned to Ethicon, Inc., describes a copolyester comprising the reaction product of a polycondensation polyester and at least one lactone, wherein the polycondensation polyester comprises the reaction product of diglycolic acid and/or a derivative thereof and ethylene glycol. The product described in this reference is useful for adhesion prevention. The copolyester described in this reference is fully amorphous with relatively low molecular weight.

U.S. Pat. No. 5,644,002 also assigned to Ethicon, Inc., describes absorbable polymers and blends of polycondensation polyester and aliphatic polyesters based on lactone monomers, where the polycondensation polyester is the reaction product of diglycolic acid and an alcohol selected from selected from the group consisting of glycerol, pentaerythritol, trimethylolpropane, hydroxyl terminated poly(ethylene glycol)s, ethylene glycol, 1,2-propanediol, 1,3-propanediol, 1,4-butylene glycol, dipropylene glycol, 1,5-pentanediol, 1,6-hexanediol, 1,7-heptanediol, and 1,8-octanediol. The absorbable polymers described in this reference are branched or crosslinked fully amorphous soft materials.

U.S. Pat. Nos. 4,048,256, 4,095,600 and 4,122,129, assigned to American Cyanamid Company, describe biocompatible and absorbable polycondensation polyesters, which are the polycondensation product of diglycolic acid and glycols such as ethylene glycol, diethylene glycol, 1,2-propylene glycol, 1,3-propylene glycol, and the like. Specifically, U.S. Pat. No. 4,095,600 describes a transesterification reaction product of (a) about 2 to 50% by weight of a polycondensation polyester made of diglycolic acid and an unhindered glycol and (b) polyglycolic acid (PGA) of molecular weight above 30,000 Daltons before reaction. Although it is believed that the transesterification reaction product described in this reference exhibits crystallinity, the absorbability thereof is not expected to be very good due to the high melting point of the PGA moieties.

Therefore, there remains a need for a synthetic absorbable polymer that will achieve faster absorption or hydrolysis, while preserving mechanical strength that is required, for example, for surgical sutures, and that may be used to produce microspheres for use as an injectable composition or drug delivery carrier.

SUMMARY OF THE INVENTION

Described herein are a composition comprising a semi-crystalline, absorbable copolyester comprising the reaction product of a polycondensation polyester and at least one lactone, wherein the polycondensation polyester comprises the reaction product of diglycolic acid and/or a derivative thereof and diethylene glycol; and the copolyester comprises about 30 to 60% by weight of the polycondensation polyester based on the total weight of the copolyester; absorbable medical devices including without limitation sutures, meshes and microspheres comprising such copolyesters; and a method of making of absorbable microspheres.

Also described herein is a method of melt blowing an absorbable copolyester composition. The method comprises the steps of providing an absorbable copolyester composition to an extruder, the absorbable copolyester composition comprising an absorbable copolyester comprising the reaction product of a polycondensation polyester and at least one lactone monomer, wherein the polycondensation polyester comprises the reaction product of diglycolic acid and/or a derivative thereof and diethylene glycol; the copolyester comprising about 30 to about 60% by weight of the polycondensation polyester based on the total weight of the copolyester; the copolyester having a crystallinity ranging from about 10 to about 50%; extruding the polymeric composition through a die assembly, the die assembly having a plurality of spinnerets, to form filament strands; attenuating the filament strands with hot air to form microfibers; collecting the microfibers on a collector screen; and cooling and solidifying the microfibers to form a nonwoven web.

DETAILED DESCRIPTION

The present invention relates to a composition comprising a semi-crystalline, absorbable copolyester of a polycondensation polyester and at least one lactone, more specifically, a semi-crystalline absorbable copolyester comprising the reaction product of poly(ethoxyethylene diglycolate) (PEEDG) and at least one lactone, where the copolyester comprises about 30 to 60% by weight, preferably about 30 to 50% by weight, of the poly(ethoxyethylene diglycolate) based on the total weight of the copolyester.

In one embodiment of the present invention, the copolyester comprises the reaction product of a polycondensation polymer and at least one lactone, wherein the polycondensation polyester comprises the reaction product of diglycolic acid and/or a derivative thereof and diethylene glycol.

In another embodiment, the polycondensation polyester comprises the reaction product of diglycolic acid and/or a derivative thereof, up to about 25 mole percent of an aliphatic diacid based on the total moles of acid, and diethylene glycol. Specifically, the aliphatic diacid may be an aliphatic alpha-omega dicarboxylic acid, including but not limited to 3,6-dioxaoctanedioic acid, 3,6,9-trioxaundecanedioic acid, and combinations thereof.

The polycondensation polyester may be synthesized by conventional techniques. For example, in a condensation polymerization, diglycolic acid and diethylene glycol may be polymerized in the presence of a catalyst at elevated temperatures and reduced pressures. A variety of catalysts may be used, but organometallic compounds have been found to be useful. The catalyst for the polycondensation step of the synthesis is preferably tin based, e.g., stannous octoate. The most desirable catalyst is dibutyltin oxide and is present in the diglycolic acid/diethylene glycol monomer mixture at a sufficiently effective molar ratio of monomer to catalyst, e.g., ranging from about 5,000/1 to about 100,000/1. For example, the ratio of 10,000/1 has been found to be quite suitable. The reaction is typically carried out at a temperature range from about 100° C. to about 220° C., preferably from about 140° C. to about 180° C., under an inert atmosphere until esterification of diglycolic acid is complete. Preferably, 165° C. has been found to be a desirable reaction temperature when employing a vertically stirred reactor. It should be noted that the optimum reaction temperature may be reactor and catalyst level dependent but can be found by one having only ordinary skill through the use of experiments. The first stage of the polycondensation reaction (inert gas at atmospheric pressure) is followed by polymerization under reduced pressure until the desired molecular weight and viscosity are achieved.

In the case of medical devices that are required to exhibit mechanical strength, the weight average molecular weight of the polycondensation polymer can range from about 20,000 to about 50,000 g/mol, preferably from about 30,000 to about 50,000 g/mol, most preferably about 40,000 g/mol. This corresponds to an inherent viscosity range from about 0.68 to about 1.0 dL/g. When the molecular weight of the polycondensation polymer is lower than about 20,000 g/mol, the molecular weight of the final copolyester is too low to achieve the desired mechanical properties, for example, for suture applications. Although molecular weight can be increased with increasing reaction time, it becomes increasingly difficult to achieve very high molecular weight. We have found, in general, that a molecular weight of the polycondensation polymer greater than about 50,000 g/mol, is not necessary to achieve desirable properties. One could however envision that this value is not an absolute bar. One might for instance, increase the molecular weight of the polycondensation polymer, and lower the amount of the lactone monomer used in the preparation of the final copolyester. In the case of microspheres, the weight average molecular weight of the polycondensation polymer can range from about 5,000 to about 15,000 g/mol, preferably from about 8,000 to about 12,000 g/mol, most preferably about 10,000 g/mol. This corresponds to an inherent viscosity range from about 0.30 to about 0.40 dL/g. When the molecular weight of the polycondensation polymer is lower than about 5,000 g/mol, the molecular weight of the final copolyester is too low to achieve the desired mechanical properties. In general, a molecular weight of the polycondensation polymer greater than about 15,000 g/mol is unnecessary to achieve desirable properties. One could however envision that this value is not an absolute bar. One might for instance, increase the molecular weight of the polycondensation polymer, and lower the amount of the lactone monomer used in the preparation of the final copolyester.

PEEDG is a fully amorphous polycondensation product of diglycolic acid and diethylene glycol. When the diethylene glycol is used in excess, the resultant polycondensation product contains hydroxyl-capped end groups, and is then capable of serving as a macroinitiator in the subsequent, second stage ring-opening polymerization with a lactone monomer, such as glycolide. When PEEDG is reacted with lactone monomers such as glycolide and transesterification reactions are minimized, block glycolide sequences form and the resultant copolyester is a crystallizable material. More specifically, this results in a semi-crystalline copolyester, having properties that are particularly advantageous for example in fiber manufacturing processes. Additionally, the crystallization rate of the copolyester is observed to be fast, which is another advantageous property, for example, in fiber manufacturing processes. Finally, both the PEEDG and the copolyester product derived therefrom are hydrophilic and fast-absorbing polymers.

The amount of polycondensation polyester used to prepare the copolyester of the present invention ranges from about 30 to 60% by weight, preferably about 30 to 50% by weight based on the total weight of the copolyester.

Suitable lactone monomers that may be reacted with the polycondensation polyester include, but are not limited to, glycolide, lactide (l, d, dl, meso), p-dioxanone, trimethylene carbonate, epsilon-caprolactone, delta-valerolactone, beta-butyrolactone, epsilon-decalactone, 2,5-diketomorpholine, pivalolactone, alpha,alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations of two or more thereof. The preferred lactone monomer includes glycolide.

In one embodiment, the copolyester may comprise the reaction product of a polycondensation polyester such as poly(ethoxyethylene diglycolate) and a lactone such as glycolide.

In another embodiment, the copolyester may comprise the reaction product of a polycondensation polyester and two or more lactones. For example, the copolyester may comprise the reaction product of the polycondensation polyester, at least 75 mole percent glycolide based on the total moles of lactone, and a second lactone monomer.

The copolyesters of the present invention may be conveniently synthesized by reaction of a dihydroxy poly(alkylene diglycolate) homopolymer or copolymer with a lactone by conventional techniques using conventional processes. For example, the polycondensation polyester is used as an α,ω-dihydroxy macroinitiator in a subsequent ring opening polymerization (ROP) with a lactone or a lactone mixture. The lactone monomers are copolymerized into the polycondensation polyester in the presence of a conventional organometallic catalyst at elevated temperatures. The catalyst for the ROP may be already present as residual catalyst in the polycondensation polyester or may be additional catalyst added in this second step of the synthesis. A suitable catalyst added at the time of the ROP can be an organometallic catalyst. The ring-opening organometallic catalyst is preferably tin based, e.g., stannous octoate, and is present in a sufficiently effective amount in the monomer mixture, preferably at a molar ratio of lactone monomer-to-catalyst ranging from about 20,000/1 to infinity (i.e. no additional catalyst used). Thus one might utilize a tin-IV compound such as dibutyltin oxide at a diacid, for instance, diglycolic acid-to-catalyst ratio of about 10,000/1 to prepare the polycondensation polyester and then add a tin-II compound such as stannous octoate at a lactone-to-added-catalyst molar ratio of about 240,000/1 at the time of the ring opening polymerization. The copolyesters of the present invention may be synthesized alternately with no additional catalyst being added at the time of the ROP as described in Example 2A.

In the case of medical devices that are required to exhibit mechanical strength, the ROP step can be immediately conducted in the same reactor as that used to synthesize the polycondensation polyester immediately after the completion of the polycondensation step, if the reactor can provide adequate heat transfer and agitation. The lactone or lactone mixture can be added as a solid, a slurry, or in molten form. Alternately, the ROP can be conducted in a separate reactor at a later date, or in the reactor used for the polycondensation polyester at a later date. If this is the case, the polycondensation polyester is discharged from its reactor and is stored in an environment that minimizes water pick up and hydrolysis. In the case of adding glycolide monomer, the monomer can be added as a solid. The reactor is closed and the pressure reduced. The reactor is usually held under vacuum for a prolonged period of time, for instance overnight, to allow drying. Nitrogen is then introduced into the reactor to bring the pressure to slightly greater than one atmosphere, and the purge cycle repeated for a total of three times. The temperature of the reaction mass is brought up to 130° C. Once at this temperature, the agitator is activated. The temperature is then increased to 150° C. to complete the mixing. This mixing step is essential to produce the copolyesters of the present invention as inadequate mixing tends to allow the formation of homopolymeric sequences which can then crystallize to an extent greater than optimum. To ensure that reactants are fully mixed, in-situ spectroscopic probes (such as Near-Infrared) can be conveniently used. If additional catalyst is to be added, it is typically added once the batch has been completely mixed. The temperature is quickly brought up to the final reaction temperature, with 210° C. being a most preferred temperature, and held there for typically 2 hours. The exact reaction conditions will depend on the catalyst and its level; final reaction temperatures can vary from about 195° C. to 235° C., and more preferably from about 200° C. to about 220° C. Reaction times can vary from about 30 minutes to a few hours, depending on the catalyst and its level, and is typically conducted until the desired conversion of monomer to polymer is achieved.

In the case of microspheres, additional catalysts such as stannous octoate, can be added in the ROP stage, while the temperature is quickly brought up to the final reaction temperature, and held there for typically 4-6 hours. The exact reaction conditions will depend on the catalyst and its level; final reaction temperatures can vary from about 210° C. to 240° C., and preferably from about 220° C. to 230° C. Reaction times can vary from about 4 hours to 6 hours, depending on the catalyst and its level, and is typically conducted until the desired conversion of monomer to polymer is achieved.

An alternate reaction scheme that has been employed to prepare the copolyesters of the invention has involved adding the lactone as a molten stream into the reactor. Thus the polycondensation polyester is added first, typically as a molten stream and the reactor evacuated. The reactor is heated to 130° C. Molten glycolide (or other glycolide rich mixture) at a temperature of about 100° C. is added to the reactor. Although the batch temperature drops slightly, it is quickly brought back up to 130° C. at which point mixing is started. At this point, the process that was described above is followed.

In the case where it is desirable for the medical device to exhibit tensile strength, the copolyesters of polycondensation polyester and lactones, will typically have a weight average molecular weight of about 40,000 g/mol (a.k.a. Daltons) to about 100,000 g/mol, preferably about 50,000 g/mol to about 80,000 g/mol, and more preferably about 60,000 g/mol to about 80,000 g/mol. These molecular weights are sufficient to provide an effective inherent viscosity, typically between about 1.0 to about 2.5 deciliters per gram (dL/g), preferably about 1.2 to about 2.0 dL/g, more preferably about 1.4 to about 1.8 dL/g, as measured in a 0.1 g/dL solution of hexafluoroisopropanol (HFIP) at 25° C.

In the case of microspheres, the copolyesters of polycondensation polyester and lactones, will typically have a weight average molecular weight of about 15,000 g/mol (a.k.a. Daltons) to about 30,000 g/mol, preferably about 18,000 g/mol to about 28,000 g/mol, and more preferably about 20,000 g/mol to about 26,000 g/mol. These molecular weights are sufficient to provide an effective inherent viscosity, typically between about 0.4 to about 1.0 deciliters per gram (dL/g), preferably about 0.6 to about 0.8 dL/g, more preferably about 0.6 to about 0.7 dL/g, as measured in a 0.1 g/dL solution of hexafluoroisopropanol (HFIP) at 25° C.

In the case where it is desirable for the medical device to exhibit tensile strength, the crystallinity of the copolyester described herein ranges from about 10 to about 40% crystallinity, preferably from about 20 to about 40%, and more preferably from about 20 to about 30%. In the case of microspheres, the crystallinity of the copolyester described herein ranges from about 10 to about 25% crystallinity, and preferably from about 15 to about 20%. It has been discovered that the use of diethylene glycol to prepare the polycondensation product, PEEDG, instead of ethylene glycol as described in U.S. Patent Publication 2006/0051398, results in a copolyester product that is semi-crystalline, instead of an amorphous product.

The copolyester having the weight average molecular weights described herein may be extruded into fibers or sutures for use in a surgical wound site or trauma site, or used to make other medical devices such as meshes, or used to prepare microspheres. Alternatively, articles may be molded from the copolyester described herein by various conventional injection and extrusion molding processes. For example, the copolyester may be molded to form, without limitation, sutures, meshes, films, orthopedic devices and injection molded devices. Alternatively, the copolyester may be a component of a medical device, i.e., the copolyester may form one layer of a multi-laminate hernia repair mesh, or may be suspended in a polymer solution and coated onto at least a portion of a medical device.

Generally, the microspheres described herein may be made by coacervation, solvent evaporation, and droplet extrusion with a spinning disk. Other methods of manufacture that may be utilized for formation of microspheres include but are not limited to spray coating, pan-coating, spray-drying, phase separation, emulsion polymerization, and interfacial polymerization.

Preferably, the method for making microspheres includes dissolving the copolyester described herein, having a crystallinity ranging from about 10 to 25% and a molecular weight ranging from about 15,000 to 30,000 g/mol, in a polar organic solvent to form a first solution phase, wherein the weight ratio of copolyester to the polar organic solvent may range from about 0.001 to about 1, and preferably from about 0.02 to about 0.33. Then the first solution phase may be heated to about 50° C. to about 100° C., and the preheated first solution phase may be subsequently mixed with a volatile non-polar co-solvent to form an oil phase, wherein the ratio of the volatile non-polar co-solvent to the polar solvent ranges from about 0.50 to about 30, and preferably from about 5 to about 15. The polar organic solvent is preferably DMSO and the volatile non-polar co-solvent is preferably methylene chloride. The oil phase formed above may then be transferred into an aqueous phase in a dropwise manner to form an oil in water emulsion (referring herein to a mixture of two immiscible substances), wherein the ratio of the aqueous phase to the oil phase ranges from about 1 to about 100, and preferably from 5 to about at least 15. Methods of forming the emulsion include, but are not limited to, vortexting, mixing and homogenizing.

The volatile non-polar co-solvent may then be removed from the oil/water emulsion by evaporation, followed by removal of the polar organic solvent from the oil/water emulsion. Upon drying, uniform and fine microspheres comprised of the copolyester may be formed. The microspheres described herein have a particle size ranging from about 20 to about 200 microns, and preferably from about 40 to about 100 microns, and are capable of retaining their distinct spherical shape during manufacture, storage, and physical transportation.

Optionally, the microspheres described herein may have incorporated thereon or therein a hydrophilic active agent such as tranilast and the hydrophilic analogs and derivatives thereof. Preferably, the hydrophilic active agent is tranilast. Tranilast, also known as N-(3,4-dimethoxycinnamoyl) anthranlic acid, or analogs thereof, is effective for treating inflammation, allergies and asthma, and reducing or preventing formation of adhesions between tissue surfaces in body cavities following surgical procedures when administered directly to the tissue and body cavity in amounts and under conditions effective to inhibit the formation of post-operative adhesions, as described in US Patent Application Nos. US2005/0106229A1 and US2005/0106230A1 to Cooper. The active agent may be incorporated into the first solution phase described above by dissolving the copolyester and the hydrophilic active agent in a common polar organic solvent, wherein the weight ratio of copolyester to hydrophilic drug may range from about 0.25 to about 10 and preferably from about 2 to about 5. The amount of active agent may range from about 0.5 to 50 wt. %, based on the total weight of solid microspheres.

In accordance with this disclosure a detailed description of a melt blown nonwoven process will now be described. A typical system for use in a melt blown nonwoven process consists of the following elements: an extruder, a transfer line, a die assembly, a web formation system, and a winding system.

As is well known to those skilled in the art, an extruder consists of a heated barrel with a rotating screw positioned within the barrel. The main function of the extruder is to melt the polymer pellets or granules and feed them to the next element. The forward movement of the pellets in the extruder is along the hot walls of the barrel between the flights of the screw. The melting of the pellets in the extruder results from the heat and friction of the viscous flow and the mechanical action between the screw and the walls of the barrel. The transfer line will move molten polymer toward the die assembly. The transfer line may include a metering pump in some designs. The metering pump may be a positive-displacement, constant-volume device for uniform melt delivery to the die assembly.

As may be appreciated, the die assembly is a critical element of the melt blown process. It has three distinct components: a polymer-feed distribution system, spinnerretts (capillary holes), and an air distribution system. The polymer-feed distribution introduces the molten polymer from the transfer line to distribution channels/plates to feed each individual capillary hole uniformly and is thermal controlled. From the feed distribution channel the polymer melt goes directly to the die capillary. The polymer melt is extruded from these holes to form filament strands which are subsequently attenuated by hot air to form fine fibers. During processing, the entire die assembly is heated section-wise using external heaters to attain the desired processing temperatures. The air distribution system supplies the high velocity hot air. The high velocity air is generated using an air compressor. The compressed air is passed through a heat exchange unit, such as an electrical or gas heated furnace, to heat the air to desired processing temperatures.

As soon as the molten polymer is extruded from the die holes, high velocity hot air streams attenuate the polymer streams to form microfibers. As the hot air stream containing the microfibers progresses toward the collector screen, it draws in a large amount of surrounding air that cools and solidifies the fibers. The solidified fibers subsequently get laid randomly onto the collecting screen, forming a self-bonded nonwoven web. The collector speed and the collector distance from the die nosepiece can be varied to produce a variety of melt-blown webs. Typically, a vacuum is applied to the inside of the collector screen to withdraw the hot air and enhance the fiber laying process.

The melt-blown web is typically wound onto a tubular core and may be processed further according to the end-use requirement.

While the following examples demonstrate certain embodiments of the invention, they are not to be interpreted as limiting the scope of the invention, but rather as contributing to a complete description of the invention.

Example 1

Synthesis of Hydroxy Terminated Poly(Ethoxyethylene Diglycolate) (PEEDG)

A dual-agitated reactor with intermeshing HELICONE patterned blades (D.I.T. 10CV reactor) was employed. After charging the reactor with 7.0 kg of diglycolic acid, 16.6 kg of diethylene glycol (DEG) and 1.3 grams of dibutyltin oxide catalyst, the pressure was reduced to below 1 Torr and the vacuum preserved over night. The next day vacuum was released by introducing dry nitrogen (argon can be substituted) and heating of the mixture was started, and the agitator was started and set to 15 RPM in reverse. When the reactor temperature reached 150° C., the agitator speed was reset to 20 RPM in a forward direction. Soon first distillate appeared containing mostly water, an esterification by-product. The reaction was continued at 170° C. for about 2 hours until approximately all water was distilled and/or first traces of DEG appeared in the distillate. After the first nitrogen/argon stage was completed, pressure was lowered gradually to full vacuum while the temperature of the batch was maintained at 170° C. A vacuum of about 30-50 mTorr was maintained throughout the rest of the reaction, a total time of approximately 80 hours. Melt and solution viscosities were regularly checked to ensure polycondensation polyester of a desired molecular weight. Hydroxy end-capped polycondensation polyester was discharged after approximately 66 hours (sample 1A) and 80 hours (1B) of reaction time, respectively, under vacuum. Both portions were a fully amorphous, colorless viscous liquid with a glass transition temperature of about −13.0 and −11.5° C., respectively. Weight average molecular weight was about 21,000 and 27,000 g/mol respectively; the resin sample under vacuum for 66 hours (V+66 h) exhibited an inherent viscosity (IV) of 0.69 dL/g, while the sample discharged at V+80 hours had IV of 0.84 dL/g, as determined in HFIP at 25° C. at a concentration of 0.1 g/dL.

Example 2A

Synthesis of Copolyester IA: The Copolymerization of an α,ω-Dihydroxy Poly(Ethoxyethylene Diglycolate) Homopolymer with a Lactone Monomer, Glycolide, (PEEDG/Gly 40/60)

A portion of the polycondensation polyester (7.4 kg) produced in Example 1 (V+80, sample portion "B") was held in the DIT 10CV reactor at room temperature under nitrogen. A S/S melt-tank was used to melt the crystalline glycolide, prior to the addition into the reactor with the polycondensation polyester. The glycolide (11.1 kg) was charged to the melt-tank, pulled under vacuum, and then heated and held under nitrogen at 120° C. After the polycondensation polyester was heated to approximately 120° C., at which point the molten glycolide monomer was transferred from the melt tank with agitation.

Agitator mixing was continued (20 RPM) and the batch temperature raised to 225° C. for a short period, to assure that there was no PGA "freeze-up". In situ, a real-time Fourier Transform Near-Infrared probe was used to confirm complete mixing of components. The temperature was then reduced to 210° C. and the reaction was continued for another two hours. The discharged copolyester was slightly crystalline, with a brownish to slightly yellow tint, and had a glass transition temperature of 14.5° C. Weight average molecular weight was approximately 60,000 g/mol and an inherent viscosity of 1.38 dL/g, as determined in HFIP at 25° C. at a concentration of 0.1 g/dL, was recorded. The composition was confirmed by $H^1$NMR to be 40/60 by weight poly(ethoxyethylene diglycolate-co-glycolide).

The copolymer was sized to approximately 3/16" granules in a rotating knife granulator, sieved to remove fines, and placed in a Patterson-Kelley twin-shell tumble dryer. The resin was subjected to full vacuum at ambient temperature for approx. 18 hours, at which point heat was introduced to the dryer. The dryer was heated to 110° C. for approximately 24 hours with full vacuum (<200 mtorr) at which point the heat was removed, and the vessel allowed to cool to room temperature. The resin was removed from the dryer, placed in vacuum containers and held under vacuum until further use.

The combined sources of tin in Example 2A result in a lactone-to-total-tin-catalyst ratio of about 28,300/1. The total tin in the final copolyester is about 32 ppm on a weight basis.

Example 2B

Synthesis of Copolyester IB: The Copolymerization of an α,ω-Dihydroxy Poly(Ethoxyethylene Diglycolate) Homopolymer with a Lactone Monomer, Glycolide, (PEEDG/Gly45/55)

A portion of a polycondensation polyester produced in a similar manner as described in Example 1 (8.3 kg) having weight average molecular weight of 42,500 g/mol and inherent viscosity of 1.16 dL/g, was reacted with glycolide monomer (10.1 kg) by ring-opening polymerization according to procedures described in Example 2A. Final composition revealed by NMR was PEEDG/Gly 45/55 wt. %. This copolymer is semi-crystalline, with the weight average molecular weight of 75,000 g/mol and inherent viscosity of 1.64 dL/g.

Example 2C

Synthesis of Copolyester IC: The Copolymerization of an α,ω-Dihydroxy Poly(Ethoxyethylene Diglycolate) Homopolymer with a Lactone Monomer, Glycolide, (PEEDG/Gly 50/50)

A portion of a polycondensation polyester produced in a similar manner as described in Example 1 (8.2 kg) having weight average molecular weight of 34,000 g/mol and inherent viscosity of 0.94 dL/g, was reacted with glycolide monomer (8.2 kg) by ring-opening polymerization according to procedures described in Example 2A. Final composition revealed by NMR was PEEDG/Gly 50/50 wt. %. This copolymer is semi-crystalline, with the weight average molecular weight of 55,000 g/mol and inherent viscosity of 1.35 dL/g.

Example 3

Synthesis of Copolyester II: (PEEDG/Gly 30/70)

A portion of the polycondensation polyester produced as described in Example 1 (1.8 kg) having weight average molecular weight of 21,000 g/mol and inherent viscosity of 0.69 dL/g (V+66 h, sample portion "A"), was reacted with glycolide monomer (4.2 kg) by ring-opening polymerization according to procedures described in Example 2A. Final composition revealed by NMR was PEEDG/Gly 30/70 wt. %. This copolymer is semi-crystalline, with the weight average molecular weight of 42,000 g/mol and inherent viscosity of 1.18 dL/g.

Example 4

Synthesis of Copolyester III (PEEDG/Gly 40/60)

A portion of the polycondensation polyester produced as described in Example 1 (6.1 kg) having weight average molecular weight of 12,700 g/mol and inherent viscosity of 0.35 dL/g, was reacted with glycolide monomer (9.1 kg) by ring-opening polymerization according to procedures described in Example 2A. The final composition revealed by NMR was PEEDG/Gly 40/60 wt. %. This copolymer is semi-crystalline, with the weight average molecular weight of 24,000 g/mol and inherent viscosity of 0.80 dL/g.

Example 5

Synthesis of Copolyester IV (PEEDG/Gly 30/70)

A portion of the polycondensation polyester produced as described in Example 1 (4.1 kg) having weight average molecular weight of 12,700 g/mol and inherent viscosity of 0.35 dL/g, was reacted with glycolide monomer (9.5 kg) by ring-opening polymerization according to procedures described in Example 2A. The final composition revealed by NMR was PEEDG/Gly 30/70 wt. %. This copolymer is semi-crystalline, with the weight average molecular weight of 24,000 g/mol and inherent viscosity of 0.79 dL/g.

Example 6

Melt index testing was conducted on several PEEDG/Gly copolymers to determine their melt properties suitable for fiber extrusions. Melt index testing was performed on Melt Index Plastometer (manufactured by Tinius & Olsen, Willow Grove, Pa., USA). The procedure is described as follows. The material to be tested is inserted into the bore of a preheated Plastometer (e.g. 195-235° C.) containing the designated die. A piston rod containing a known weight (e.g. 3,700 g) is placed on the top of the polymer. The weight forces the melted polymer to flow through a die of predetermined length and diameter at the preset temperature (e.g. 195-235° C.), which is above the melting point of the polymer.

Next, the portions of extruded polymers, obtained at designated time intervals, are accurately weighed to determine a weight per unit of time measurements. Melt index (MI) is generally defined as grams of polymers that are collected through the die for the time of 10 minutes. Using this method, accurate comparisons can be made to evaluate the flow characteristics of similar or different polymers at constant conditions.

TABLE 1

Melt index test of different PEEDG/Gly copolymers.

| Copolymer ID | Composition | Mw (g/mol) | Tm (° C.) | Condition | Melt index, MI (g/10 min) |
|---|---|---|---|---|---|
| Copolyester IA | PEEDG/Gly 40/60 | 60,000 | 192 | T = 235° C., w = 3,700 g | 1.039 |
| | | | | T = 200° C., w = 3,700 g | 0.372 |
| Copolyester IB | PEEDG/Gly 45/55 | 75,000 | 198 | T = 235° C., w = 3,700 g | 0.560 |
| | | | | T = 225° C., w = 3,700 g | 0.417 |
| Copolyester IC | PEEDG/Gly 50/50 | 55,000 | 197 | T = 225° C., w = 3,700 g | 0.762 |
| Copolyester II | PEEDG/Gly 30/70 | 42,000 | 205 | T = 235° C., w = 3,700 g | Failed |
| | | | | T = 210° C., w = 3,700 g | 1.075 |
| | | | | T = 210° C., w = 3,700 g | No flow |
| Copolyester III | PEEDG/Gly 40/60 | 24,000 | 188 | T = 225° C., w = 3,700 g | Failed |
| | | | | T = 195° C., w = 3,700 g | Failed |
| Copolyester IV | PEEDG/Gly 30/70 | 24,000 | 195 | T = 200° C., w = 3,700 g | Failed |

"Failed" MI samples indicate that melt viscosity is too low for these materials to be measured. This indirectly implies that these copolyesters cannot be extruded into fibers. Data for Copolyester II indicate that only extrusion at low temperature melt conditions (slightly above its melting point) may have suitable melt viscosity.

Example 7

Crystallization properties of several PEEDG/Gly copolyesters were determined using differential scanning calorimetry (DSC). Overall crystallization rates depend principally on two factors: the concentration of growing spherulites over time (nucleation rate) and the rate of spherulitic growth. As expected, these processes have a measurable effect on calorimetric data. Calorimetric results were generated on a TA Instruments Differential Scanning Calorimeter, Model 2910 MDSC, using dry $N_2$ as a purge gas. Crystallization studies were conducted in the following manner: after melting, the sample was subjected to the cooling step from the melt at a constant cooling rate of 10° C./min. Crystallization is manifested by the exothermic peak, whose high temperature slope is used to determine crystallization rate, while the area under the peak (heat of crystallization, $\Delta H_C$) is associated with the overall level of crystallinity.

TABLE 2

Crystallization properties of PEEDG/Gly copolyesters

| Copolyester ID | Composition | IV (dL/g) | $T_{cryst}$ (° C.) | $\Delta H_c$ (J/g) | Cryst. Rate (W/g/° C.) |
|---|---|---|---|---|---|
| Copolyester IA | PEEDG/Gly 40/60 | 1.38 | 137.0 | 39.5 | −0.0342 |
| Copolyester IB | PEEDG/Gly 45/55 | 1.64 | 102.0 | 7.5 | −0.0008 |
| Copolyester IC | PEEDG/Gly 50/50 | 1.35 | 95.0 | 2.0 | −0.0003 |
| Copolyester II | PEEDG/Gly 30/70 | 1.18 | 145.5 | 41.0 | −0.0370 |
| Copolyester III | PEEDG/Gly 40/60 | 0.80 | 119.5 | 42.5 | −0.0166 |
| Copolyester IV | PEEDG/Gly 30/70 | 0.79 | 101.5* | 12.5 | −0.0018 |

*another smaller crystallization peak observed at 205° C.

Data in Table 2 suggest that the copolyesters described herein can crystallize under the specified cooling conditions from the melt (−10° C./min). Polymers with higher molecular weight and faster crystallization kinetics may be easy to extrude into fibers. In the case of copolyesters having low molecular weight and that crystallize slowly, such as copolyesters III and IV, it is not expected that these can be extruded into fibers. Therefore, for the copolyester to be extruded into fibers, first the copolyesters must have a suitable melt viscosity (MI) or sufficiently high molecular weight, and second, the copolyesters must have relatively fast crystallization kinetics.

Example 8

2/0 Monofilaments Produced from Copolyesters IA-C

Monofilaments 2/0 were made from Copolyesters IA-C as described above using cold drawing procedure under following processing conditions:

Die temperature: 200° C. (Fiber-IA); 225° C. (Fiber-IB); 207° C. (Fiber-IC);

Water bath temperature: 20° C. (Fiber-IA); 40° C. (Fibers-IB&C);

Speed of the first set of Godets for all fibers (not heated): 15 RPM

Speed of the second set of Godets for all fibers (not heated): 100 RPM

Speed of the third set of Godets for all fibers (not heated): 110 RPM

Overall draw ratio for all fibers were 7.2

First oven temperature: 80° C. (Fiber-IA); 110° C. (Fiber-IB); 90° C. (Fiber-IC);

Second oven temperature: 95° C. (Fiber-IA); 110° C. (Fiber-IB); 100° C. (Fiber-IC);

Monofilaments appear to be smooth, pliable yet strong.

Selected thermal properties of the fibers are determined using differential scanning calorimetry, and are listed in Table 3.

TABLE 3

Thermal and crystallization properties of the neat resin and of the selected experimental monofilaments

| Polymer | Fiber Tensile Strength (lbs) | Tm (° C.) | ΔHm (g/mol) | Tc* (° C.) | ΔHc* (g/mol) | Cryst. Rate* (W/g/° C.) |
|---|---|---|---|---|---|---|
| Neat resin IA | N/A | 196.0 | 24.0 | 137.0 | 39.5 | −0.034 |
| Fiber-IA | 13 | 193.5 | 22.0 | 132.0 | 37.5 | −0.031 |
| Neat resin IB | N/A | 198.0 | 25.0 | 102.0 | 7.5 | −0.0008 |
| Fiber-IB | 15 | 193.5 | 27.0 | 95.0 | 11.0 | −0.0011 |

*data obtained from the cooling from the melt with the constant cooling rate of 10° C./min DSC data indicate that the copolyesters (IA and IB) extruded under the conditions described above did not randomize appreciably compared to the original copolyester (neat resin), and did not loose ability to crystallize fast (compared to the neat resin), as indicated from the crystallization rates in Table 3.

Example 9

Tensile properties were determined using Instron testing machine on the unannealed monofilaments (Fiber-IA and Fiber-IC) and annealed monofilament Fiber-IB (105° C. for 6 hours). Sample rate was 20 pts/secs with crosshead speed of 12 in/min; full scale load range=100 lbf. In Table 4, selected tensile properties (mean values) are given for Fiber-IA, Fiber-IB, and Fiber-IC and for the same fibers with a single knot made in the middle of the thread.

TABLE 4

Selected Tensile properties of unannealed Fiber-IA and Fiber-IC and annealed Fiber-1B

| Sample | Diameter (mil) | Load at the break (lbs) | Stress at max load (kpsi) | Elongation (%) | Young's Modulus (kpsi) |
|---|---|---|---|---|---|
| Fiber-IA | 14.4 | 12.8 | 78.2 | 29.6 | 347 |
| Fiber-IA with a knot | 14.4 | 9.3 | NA | NA | NA |
| Fiber-IB | 12.9 | 15.0 | 112 | 56.0 | 164 |
| Fiber-IB with a knot | 12.9 | 9.7 | NA | NA | NA |
| Fiber-IC | 12.8 | 11.8 | 91.0 | 58.0 | 43 |
| Fiber-IC with a knot | 12.8 | 6.4 | NA | NA | NA |

As Table 4 indicates, excellent mechanical properties are observed for both unannealed fibers (Fiber-IA and Fiber-IC), and annealed Fiber-IB. More significantly, substantial knot security was maintained (55 to 73% of the strength) for all samples as indicated in the Table 4.

Example 10

Synthesis of Copolyester V: The Synthesis of an α,ω-Dihydroxy Poly(Ethoxyethylene Diglycolate) Homopolymer with a Lactone Monomer, Glycolide, (PEEDG/Gly 40/60)

A portion of hydroxy end-capped polycondensation polyester, produced in a similar manner as described in Example 1, is used in this example. The discharge is a fully amorphous, colorless viscous liquid with a glass transition temperature of about −15.0° C. Weight average molecular weight was about 14,000 g/mol (IV=0.35) respectively.

In the second stage, a portion of the polycondensation polyester (2.56 kg) produced as above was held in the DIT 10CV reactor at room temperature under nitrogen. A stainless steel melt-tank was used to melt the crystalline glycolide, prior to the addition into the reactor with the polycondensation polyester to be added later in a liquid state. The glycolide (3.84 kg) was charged to the melt-tank, pulled under vacuum, and then heated and held under nitrogen at about 120° C. After the polycondensation polyester was heated to approximately 120° C., the stannous octoate solution (0.417 ml in Toluene) was added in the reactor, and the molten glycolide monomer was transferred from the melt tank with agitation. Agitator mixing was continued (20 RPM) and the batch temperature raised to 240° C. for a short period, to assure that there was no PGA "freeze-up". In situ, a real-time Fourier Transform Near-Infrared probe was used to confirm complete mixing of components. The temperature was then reduced to 220° C. and the reaction was continued for another four hours. The discharged copolyester was slightly crystalline, with a brownish to slightly yellow tint, and had a glass transition temperature of 12.5° C. Weight average molecular weight was approximately 24,000 g/mol and an inherent viscosity of 0.68 dL/g, as determined in HFIP at 25° C. at a concentration of 0.1 g/dL, was recorded. The material is semi-crystalline with the melting point of about 160° C. The overall crystallinity was about 20%. The composition was confirmed by $H^1$NMR to be 40/60 by weight poly(ethoxyethylene diglycolate-co-glycolide). The copolymer was sized and dried as described in Example 2A.

Example 11

Microsphere Preparation from Copolyester V

About 2 grams of the copolyester V described in Example 10 was dissolved completely in about 8 grams of dimethyl sulfoxide, DMSO (Fluka, USA) at room temperature using magnetic stirring to make a stock solution of copolyester and DMSO. Next, the specific amounts of co-solvent methylene chloride, $CH_2Cl_2$ (Aldrich, USA), shown in Table 5, were quickly transferred by a syringe into 0.5 g of preheated (1 minute in oven at 90° C.) stock solution that was previously supplemented with additional amounts of DMSO (as shown in Table 5) and accompanied by vigorous mixing (i.e. shaking the whole mixture for 10 to 15 seconds) to reach the homogenous state. While the solution of copolyester, DMSO and methylene chloride stayed perfectly clear, using a new 1 ml syringe, the whole amount (1 ml) was slowly injected (drop-by-drop) into a 20 cc vial containing 10 grams of 3% wt. polyvinyl alcohol (PVA)/deionized water solution (10/1 water/oil ratio). The PVA/water solution was continuously mixed by a magnetic stir bar, producing a vortex at its surface. The exact amounts of solvents used to add to 0.5 g of stock solution of PEEDG/Gly 40/60 in DMSO are given in Table 5. The ratio of $CH_2Cl_2$/DMSO ranged from 2.28 to 10.

TABLE 5

| Additional DMSO (grams) | Polymer in DMSO (wt. %) | $CH_2Cl_2$ (g) | $CH_2C_2$/ DMSO Overall ratio | Wt. % Solids | Time to observe first sign of cloudiness (min) |
|---|---|---|---|---|---|
| 0.0 | 20 | 0.91 | 2.28 | 7.08 | 0.4 |
| 0.5 | 10 | 2.05 | 2.28 | 3.28 | 1.2 |
| 1.0 | 7 | 3.19 | 2.28 | 2.13 | 2.1 |
| 1.5 | 5 | 4.32 | 2.28 | 1.58 | 2.8 |
| 2.0 | 4 | 5.47 | 2.28 | 1.25 | 2.0 |
| 2.5 | 3 | 6.61 | 2.28 | 1.04 | 4.8 |
| 0.0 | 20 | 2.00 | 5.0 | 4.17 | 0.2 |
| 0.5 | 10 | 4.50 | 5.0 | 1.85 | 1.1 |
| 1.0 | 7 | 7.00 | 5.0 | 1.19 | 2.0 |
| 1.5 | 5 | 9.50 | 5.0 | 0.88 | 3.5 |
| 2.0 | 4 | 12.0 | 5.0 | 0.69 | 3.7 |
| 2.5 | 3 | 14.5 | 5.0 | 0.57 | 2.0 |
| 0.0 | 20 | 4.00 | 10.0 | 2.27 | 1.5 |
| 0.5 | 10 | 9.00 | 10.0 | 1.01 | 1.8 |

After injection was completed, the copolyester, DMSO and methylene chloride in PVA/water phase emulsion was flushed by a dry nitrogen flow to encourage faster methylene chloride evaporation. Using a FT-NIR fiber optic probe, it was determined that about 2 hours were needed for the complete removal of methylene chloride from the solution. The next step consisted of repetitively washing the solution with deionized water to remove DMSO. Initially, agitation was stopped to allow formed microspheres to precipitate at the bottom of a vessel. The water phase above is removed by a syringe, and replaced by deionized water. After continuous stirring for about 5-10 minutes, the process was repeated three times to ensure complete removal of DMSO. Finally, the formed microspheres were dried under vacuum at ambient temperature. As revealed by optical microscopy, the average diameter of these uniformly distributed microspheres ranged from 20 to 80 microns, depending of the percentage of solid (polymer) concentration in the oil phase. Higher percentage of polymer in oil phase seems to produce smaller size microspheres, and vise versa. Using this method, regular shape microspheres were formed in all solutions where the time without cloudiness exceeds 1 minute (the last column data in Table 5).

Example 12

Microsphere Preparation from PEEDG/Gly 40/60 (Copolyester V) and Tranilast

About 2 grams of copolyester described in Example 10 was dissolved completely in 8 grams of DMSO at room temperature under continuous stirring to make the same stock solution as described in Example 11. Tranilast (0.05 g) was mixed completely with 0.5 grams of PEEDG/Gly 40/60 and DMSO stock solution. As a next step, 4 grams of methylene chloride was quickly transferred by a syringe into a preheated (1 minute in oven at 90° C.) solution of tranilast, copolyester and DMSO accompanied by vigorous mixing, to form the oil phase. The overall ratio of $CH_2Cl_2$ to DMSO is 10. While the solution of tranilast, copolyester, DMSO and methylene chloride stayed perfectly clear, using a new 1 ml syringe, the whole amount was slowly injected (drop-by-drop) into a 3% wt. of polyvinyl alcohol (PVA)/deionized water solution (10/1 water/oil ratio). It is believed that up to 1/1 water/oil ratio can be used. The PVA/water solution was continuously mixed by a magnetic stir bar. After injection was completed, the tranilast, copolyester, DMSO and methylene chloride in PVA/water phase emulsion was flushed by a dry nitrogen flow to encourage faster methylene chloride evaporation to minimize the loss of tranilast into the water phase due to the solubility of the drug in the hydrophilic solvent, DMSO. The next step consisted of repeatedly washing the solution with deionized water to remove DMSO. Initially, agitation was stopped to allow the formed microspheres to precipitate at the bottom of a vessel. The water phase above is removed by a syringe, and replaced by deionized water. After continuous stirring for about 5-10 minute, the process was repeated three times to ensure removal of DMSO from the microspheres. Finally, the formed polymer microspheres containing tranilast were dried under vacuum at ambient temperature. Finally, uniformly distributed microspheres were formed with the average diameter of 40-80 microns by this method, as confirmed by optical microscopy.

Example 13 Comparative (Use of DMSO Only, without the Combination of $CH_2Cl_2$ and DMSO) Microsphere Preparation from Copolyester V The procedure of making microspheres was the same as described in Example 11, except methylene chloride was not used as a cosolvent. The clear solution of polymer in DMSO was slowly injected (drop-by-drop) using a 1 ml syringe into a 20 cc vial containing 10 grams of 3% wt. polyvinyl alcohol (PVA)/deionized water solution (10/1 water/oil ratio). No microspheres were formed by this method. Instead, nanoparticles of polymer dispersed into water/PVA were being detected.

Example 14 Comparative (No Preheating of the Polymer/DMSO Solution Prior to the Addition of $CH_2Cl_2$) Microsphere Preparation from Copolyester V If the stock solution of (2 g of Copolyester V/8 g of DMSO) is not heated before adding $CH_2Cl_2$, phase separation (cloudiness) occurs quickly causing large agglomerates to appear instead of microspheres as demonstrated herein. The procedure of making microspheres was similar to that described in Example 11, except the polymer/DMSO solution was not preheated prior to the addition of methylene chloride. The exact amounts of solvents used to add to 1.0 g of stock solution of Copolyester V in DMSO are given in Table 6

TABLE 6

| Additional DMSO (grams) | $CH_2Cl_2$ (g) | $CH_2Cl_2$/ DMSO Overall ratio | Polymer/ DMSO solution | Time to observe first sign of cloudiness |
|---|---|---|---|---|
| 5.0 | 13.2 | 2.28 | Cold | Less than 10 sec |
| 5.0 | 13.2 | 2.28 | Hot | More than 5 min |

An addition of methylene chloride into cold polymer/DMSO solution caused the fast precipitation (phase separation) of polymer causing solution cloudiness to be observed before the oil phase could be injected into the water/PVA solution. This consequently generates large particles to be formed instead of microspheres. Also, further dilution of polymer in the oil phase did not improve the solubility. On the other hand, when the polymer/DMSO solution was preheated according the procedure described in Example 11, the oil phase stayed clear for a longer time, allowing the fine, uniform microspheres to be produced.

Example 15 Comparative (Slow Transfer of Methylene Chloride into Polymer/DMSO Solution) Microsphere Preparation from Copolyester V The conditions are the same as in Example 14, except that methylene chloride was added slowly in cold polymer/DMSO solution with mixing in discrete steps until the overall ratio of $CH_2Cl_2$ to DMSO reach 2.28. At the end of this step, polymer precipitation from oil phase was even more excessive. Very non-homogeneous, gel-like structures were observed instead of cloudy solutions. Similarly, when methylene chloride were added slowly to the same preheated polymer/DMSO solution in the same manner as described above, similar non-homogeneous, gel-like structures were observed instead of cloudy solutions.

Example 16 Comparative (Fast Injection of the Oil Phase into Water/PVA Solution) Microsphere Preparation from Copolyester V and Tranilast Tranilast (12.5 mg) was mixed completely in 0.5 grams of Copolyester V/DMSO stock solution as described in Example 12. Next, 4 grams of methylene chloride was quickly transferred by a syringe into the preheated (1 minute in oven at 90° C.) solution of Tranilast, polymer and DMSO accompanied by vigorous mixing. The overall ratio of $CH_2Cl_2$ to DMSO was 10, and solution stayed for the time longer than 1 minute. In contrast to the step described in the Example 3 where the oil phase was injected slowly (drop-by-drop) into the 3% wt. PVA/vortexed water solution (10/1 water/oil ratio), this time the whole amount was injected quickly in a couple of seconds. The result was generation of large aggregates of polymer, and no microspheres were formed.

Example 17 Comparative (Too Slow Agitation of Water/PVA Solution) Microsphere Preparation from Copolyester V and Tranilast Tranilast (25 mg) was mixed completely in 0.5 grams of Copolyester V/DMSO stock solution as described in Example 12. Next, 4 grams of methylene chloride was quickly transferred by a syringe into the preheated (1 minute in oven at 90° C.) solution of Tranilast, polymer and DMSO accompanied by vigorous mixing. The overall ratio of $CH_2Cl_2$ to DMSO was 10, and solution stayed for the time longer than 1 minute, the oil phase was transferred drop-wise into the water phase. In contrast to Example 12, where vigorous mixing of 3% wt. PVA/water solution (10/1 water/oil ratio) was accompanied by the appearance of vortex, this time the agitation of water phase was slow and the vortex was hardly visible. The result was generation of a single large spherical ball of polymer, and no microspheres were detected.

Example 18 Comparative

About 2 grams of Copolyester IB was added in 8 grams of DMSO at room temperature under continuous stirring and under these conditions this copolyester (Copolyester IB) could not go into the solution. Then the mixture was heated at about 100° C. and only a small portion seemed to be dissolved, but once the mixture was brought to an ambient temperature, a gel structure (phase separation) quickly formed. The same procedure was repeated with a lower concentration of polymer (1 gram of polymer in 9 grams of DMSO) but the same phase separation occurred.

In a similar manner as described above, an attempt to dissolve Copolyester III in DMSO was made Copolyester III has comparable molecular weight with the Copolyester V (about 25,000 g/mol), but the overall crystallinity level of this material is relatively high (about 32%). As was the case with Copolyester IB, Copolyester III showed a very limited dissolution in DMSO with a gel like formation occurred rapidly at ambient conditions.

This example demonstrates the effect of polymer molecular weight and degree of crystallinity. Dissolution of higher molecular weight polymer and higher crystallinity polymer into DMSO, followed by treatment in a similar manner as described above in Example 11, failed to yield fine and uniform microspheres.

Example 19

Melt Blown Nonwoven Made from PEEDG/Gly 40/60

On a six-inch melt blown nonwoven line equipped with single screw extruder, a PEEDG/Gly 40/60 copolymer with weight-average molecular weight of 52,600 Daltons was extruded into melt blown nonwovens. This process involves feed the solid polymer pellets into a feeding hopper of an extruder. The extruder has a 1¼" single screw with three heating zones which gradually melt the polymer and extrude the molten polymer through a connector or transfer line.

The molten polymer is pushing into a die assembly containing many capillary holes of which emerge small diameter fibers. The fiber diameter is attenuated at the die exit as the fiber emerges using high velocity hot air. About 6 inches from the die exit is a rotating collection drum on which the fibrous web is deposited and conveyed to a wind up spool. The melt blown line is of standard design as described by Buntin, Keller and Harding in U.S. Pat. No. 3,978,185. The die used had 210 capillary holes with a diameter of 0.014 inch per hole. The processing conditions and resulted properties of melt blown nonwovens are listed in the following Table 7.

TABLE 7

| | Sample | | |
|---|---|---|---|
| | 1 | 2 | 3 |
| Processing Conditions: | | | |
| Die Temperature (° C.) | 234 | 245 | 245 |
| Die Pressure (psi) | 620 | 620 | 620 |
| Air Temperature (° C.) | 230 | 230 | 230 |
| Air Pressure (psi) | 14 | 14 | 14 |
| Extruder Speed (rpm) | 6.1 | 6.2 | 6.2 |
| Throughput (grams/hole/minute) | 0.217 | 0.217 | 0.217 |
| Collector Speed (meters/minute) | 4.26 | 2.12 | 1.40 |
| Nonwoven Properties: | | | |
| Base Weight (gsm) | 34 | 69 | 104 |
| Fiber Diameter (μm) | 2.5-5.0 | 2.5-5.0 | 2.5-5.0 |
| Bust Strength (psi) | 14.5 | 19.00 | 24.00 |
| Peak Tensile (N) | 19.2 | 34.2 | 36.3 |
| Air Permeability (CFM) | 125.2 | 35.2 | 22.7 |
| Average Pore Size (μm) | 19.0 | 11.7 | 11.7 |

Crystallization rate was obtained by DSC using a constant cooling rate of 10° C./min. The sample size was about 3 to 10 mg. Thermal analysis of the PEEDG/Gly 40/60 resin conducted by DSC showed a melting point of 200.5° C., and a heat of fusion of 30 J/g. The corresponding nonwoven melt blown construct made from this copolymer, and annealed at 60° C. for 12 hours, showed melting point of 201.5° C., and the heat of fusion of 32 J/g. WAXD analysis of the nonwoven construct revealed a crystallinity of 33%.

Although this invention has been shown and described with respect to detailed embodiments thereof, it will understood by those skilled in the art that various changes in form and detail thereof may be made without departing from the spirit and scope of the claimed invention.

What is claimed is:

1. A method of melt blowing an absorbable copolyester composition, comprising the steps of:
   (a) providing an absorbable copolyester composition to an extruder, the absorbable copolyester composition comprising the reaction product of a polycondensation polyester and at least one lactone monomer, wherein the polycondensation polyester comprises the reaction product of diglycolic acid and/or a derivative thereof and diethylene glycol; the copolyester comprising about 30 to about 60% by weight of the polycondensation polyester based on the total weight of the copolyester; the copolyester having a crystallinity ranging from about 10 to about 50%;
   (b) extruding the polymeric composition through a die assembly, the die assembly having a plurality of spinnerets, to form filament strands;
   (c) attenuating the filament strands with hot air to form microfibers;
   (d) collecting the microfibers on a collector screen; and
   (e) cooling and solidifying the microfibers to form a nonwoven web.

2. The method according to claim 1, wherein the at least one lactone monomer is glycolide.

3. The method according to claim 1, wherein the copolyester comprises the reaction product of a polycondensation polyester, at least 75 mole percent glycolide based on the total moles of lactone, and a lactone selected from the group consisting of lactide (l, d, dl, meso), p-dioxanone, trimethylene carbonate, epsilon-caprolactone, delta-valerolactone, beta-butyrolactone, epsilon-decalactone, 2,5-diketomorpholine, pivalolactone, alpha,alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicyclooctane-7-one, and combinations thereof.

4. The method according to claim 1, wherein the polycondensation polyester comprises the reaction product of diglycolic acid and/or a derivative thereof, up to about 25 mole percent of an aliphatic diacid based on the total moles of acid, and diethylene glycol.

5. The method according to claim 1, wherein the weight average molecular weight of the copolyester is from about 25,000 to about 70,000 g/mol.

6. The method according to claim 1, wherein weight average molecular weight of the copolyester is from about 30,000 to about 60,000 g/mol.

7. The method according to claim 1, wherein weight average molecular weight of the copolyester is about 40,000 to about 55,000 g/mol.

8. The method according to claim 1, wherein weight average molecular weight of the polycondensation polymer is from about 10,000 to about 25,000 g/mol.

9. The method according to claim 1, wherein weight average molecular weight of the polycondensation polymer is from about 15,000 to about 20,000 g/mol.

10. A nonwoven construct comprising an absorbable copolyester composition comprising the reaction product of a polycondensation polyester and at least one lactone monomer, wherein the polycondensation polyester comprises the reaction product of diglycolic acid and/or a derivative thereof and diethylene glycol;
the copolyester comprising about 30 to about 60% by weight of the polycondensation polyester based on the total weight of the copolyester;
the copolyester having a crystallinity ranging from about 10 to about 50%, and said nonwoven construct comprising microfibers having a diameter ranging from 1 to 8 μm.

11. The nonwoven construct of claim 10, wherein the at least one lactone monomer is glycolide.

12. The nonwoven construct of claim 10, wherein the copolyester comprises the reaction product of a polycondensation polyester, at least 75 mole percent glycolide based on the total moles of lactone, and a lactone selected from the group consisting of lactide (l, d, dl, meso), p-dioxanone, trimethylene carbonate, epsilon-caprolactone, delta-valerolactone, beta-butyrolactone, epsilon-decalactone, 2,5-diketomorpholine, pivalolactone, alpha,alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 1,4-dioxan-2-one, 6,8-dioxabicycloctane-7-one, and combinations thereof.

13. The nonwoven construct of claim 10, wherein the polycondensation polyester comprises the reaction product of diglycolic acid and/or a derivative thereof, up to about 25 mole percent of an aliphatic diacid based on the total moles of acid, and diethylene glycol.

14. The nonwoven construct of claim 10, wherein the weight average molecular weight of the copolyester is from about 25,000 to about 70,000 g/mol.

15. The nonwoven construct of claim 10, wherein weight average molecular weight of the polycondensation polymer is from about 10,000 to about 25,000 g/mol.

* * * * *